United States Patent [19]
Cho

[11] Patent Number: 5,572,370
[45] Date of Patent: Nov. 5, 1996

[54] APPARATUS FOR DETERMINING FERTILE PERIODS

[76] Inventor: Casey Cho, 420 Pilgrim Pl., San Marino, Calif. 91108

[21] Appl. No.: 451,684

[22] Filed: May 26, 1995

[51] Int. Cl.⁶ ................................................. G02B 21/00
[52] U.S. Cl. ..................... 359/801; 359/379; 359/385; 359/390; 359/804; 128/738; 422/82.05
[58] Field of Search ........................ 436/63, 65, 181, 436/811, 814; 359/379, 385, 798, 799, 801, 803, 804, 806, 389, 390; 128/738; 422/82.05

[56] References Cited

U.S. PATENT DOCUMENTS

| | | | |
|---|---|---|---|
| 3,582,181 | 6/1971 | Dolores et al. | 359/379 |
| 4,815,835 | 3/1989 | Corona | 359/379 |
| 4,847,206 | 7/1989 | Heinz | 436/63 |
| 5,062,697 | 11/1991 | Mitchell | 359/379 |

FOREIGN PATENT DOCUMENTS

| | | | |
|---|---|---|---|
| 2059681 | 10/1992 | Canada | 128/738 |
| 528100 | 2/1994 | European Pat. Off. | |
| 2062276 | 5/1981 | United Kingdom | |
| 4528130 | 10/1995 | WIPO | |

OTHER PUBLICATIONS

R. M. Lequin et al. Clin Chem. 1986, 32, 831–834.
O. Kogbe et al. Medline Abstract, AN 92036456.
L. Rotta et al. Medline Abstract, AN 93008339.
A. P. Andonopouls et al. Medline Abstract, AN93059007.
M. Guida et al, Medline Abstract, AN93215108.
M. Barbato et al. Medline Abstract, AN94197039.
B. Berardono et al. Medline Abstract, AN94225875.

Primary Examiner—Arlen Soderquist
Attorney, Agent, or Firm—J. E. Brunton

[57] ABSTRACT

A compact, self-contained, easy-to-use and readily portable apparatus which can be carried in a woman's purse or pocket for determining the period of maximum fertility. The apparatus includes a hollow housing that sealably contains a small magnifying system, a saliva specimen slide and an internal switch operated illuminating system for illuminating the saliva slide. The small magnifying system is used to closely view patters formed on the specimen slide by the saliva after it has dried and crystallized on the slide. The patterns are then compared with standard comparison patterns to determine the woman's present ability to conceive.

9 Claims, 3 Drawing Sheets

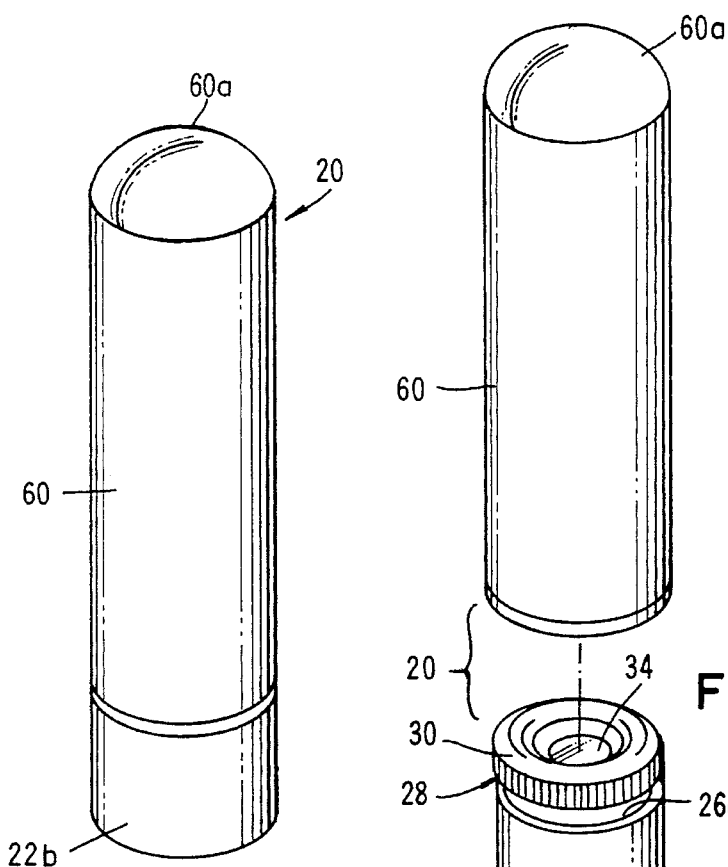
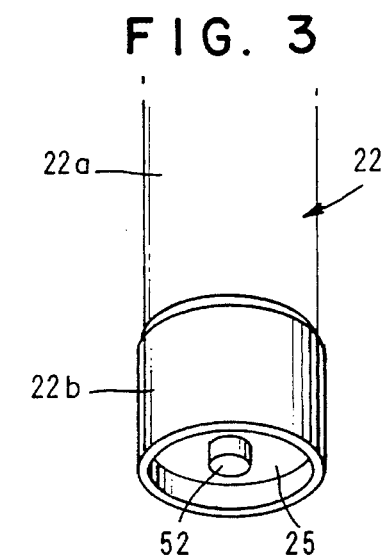
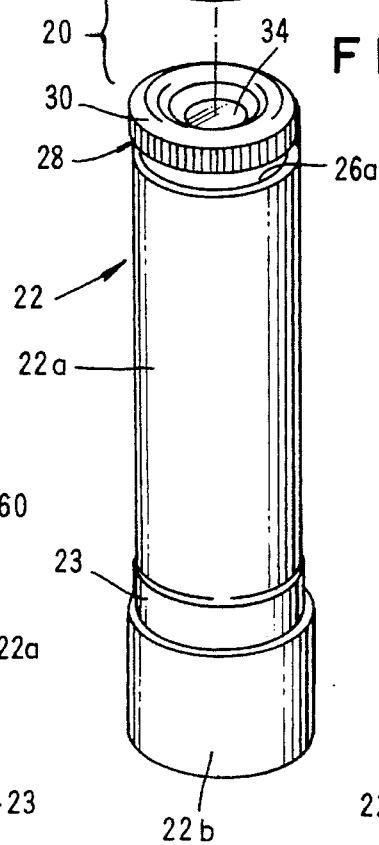
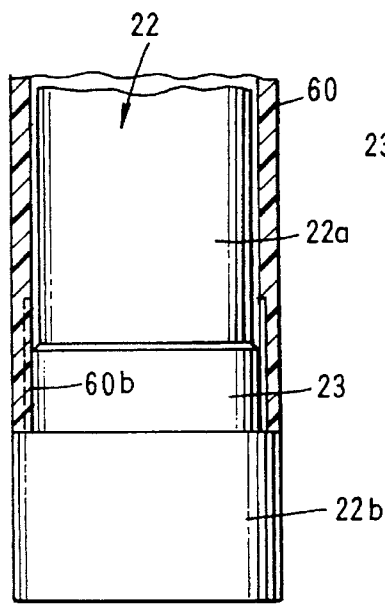
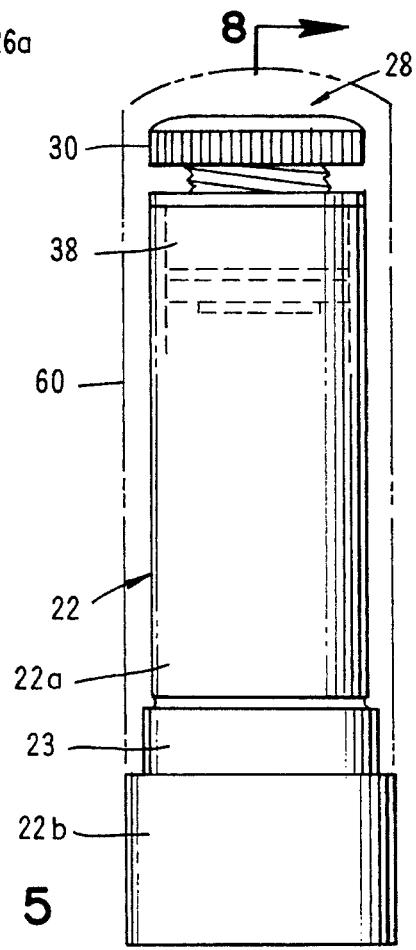

INFERTILE

TRANSITION

FERTILE 5,572,370

APPARATUS FOR DETERMINING FERTILE PERIODS

BACKGROUND OF THE INVENTION

1. Field of the Invention

The present invention relates generally to fertility testing of women. More particularly, the invention concerns a small, easily portable magnification apparatus for viewing crystallized saliva deposited on a small, built-in object slide to identify crystalline patterns which are directly related to fertility.

2. Discussion of the Invention

One widely agreed upon barometer for assessing women's fertile days is the basal body temperature. For example, it has been demonstrated that shortly after menstruation begins the temperature is low and that, once the egg is released, the temperature goes up. Vaginal secretions also change and, during the period of maximum fertility, the secretions being extremely viscous. However, body temperature and secretion viscosity measurements have proven somewhat unreliable in accurately determining fertile periods.

In addition to body temperature and secretion viscosity measurements for determining fertility, it has been known for sometime in the medical community that by studying a woman's saliva under high magnification, it is possible to determine periods of maximum fertility, More specifically, it has been demonstrated in the laboratory that by observing the crystallized saliva of the woman under high magnification, identifiable patterns or structures can be observed which relate directly to the likelihood of conception should intercourse occur. These patterns, which are readily observable under the laboratory microscope, are believed to relate to hormonal and mineral changes which occur in women during their menstrual cycle. When the woman is most fertile, that is most likely to conceive, the saliva dries in fern-like patterns. However, during non-fertile periods, the saliva pattern is random and generally unconnected dots appear on the object slide carrying the dried saliva. When a combination of dots and fern-like patterns appear, the woman is in a transitional period, that is, a period when conception is possible, but not highly likely. As a general rule laboratory tests have shown that the fern-like structures appear approximately three to four days prior to ovulation and end two to three days after ovulation.

SUMMARY OF THE INVENTION

It is an object of the present invention to provide a compact, self-contained, easy-to-use and readily portable apparatus which can be carried in a woman's purse or pocket for determining the period of maximum fertility and the method of using the apparatus.

It is another object of the invention to provide an apparatus of the aforementioned character having a hollow housing, which is relatively small, that is, nominally the size of a lipstick container, that sealably contains a small magnifying system, a saliva specimen slide and an internal switch operated illuminating system for illuminating the saliva slide.

It is another object of the invention to provide a method for accurately determining, through use of the aforementioned apparatus, the days of the woman's menstrual cycle during which she is most likely to be able to conceive.

Another object of the invention is to provide an apparatus of the character described in the preceding paragraphs in which the small magnifying system can be used to closely view patterns formed on the specimen slide by the saliva after it has dried and crystallized on the slide.

Yet another object of the invention is to provide a method for determining the period of maximum fertility using the apparatus as described in the preceding paragraph by comparing the patterns formed by the crystallized saliva on the specimen slide with standard patterns that have been determined to indicate the fertile and non-fertile conditions of the woman.

Another object of the invention is to provide a method and apparatus of the class described which can be used by lay persons in a home environment with minimum training.

BRIEF DESCRIPTION OF THE DRAWINGS

FIG. 1 is a generally perspective view of one form of the apparatus of the invention for determining fertile periods.

FIG. 2 is a generally perspective, exploded view of the apparatus of FIG. 1 showing the cover removed.

FIG. 3 is a generally perspective, fragmentary view of the bottom portion of the apparatus of FIG. 1.

FIG. 4 is a fragmentary view partly in cross section of the base portion of the apparatus showing the manner in which the cover is interconnected with the base.

FIG. 5 is an enlarged, side-elevational view of the apparatus.

DESCRIPTION OF THE INVENTION

Figure 6:
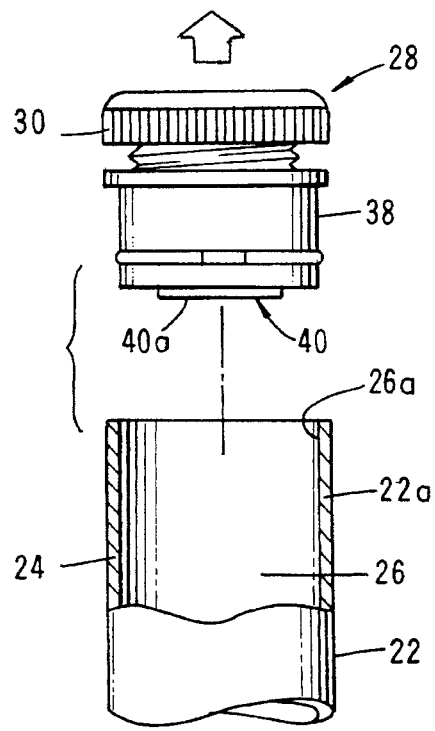
FIG. 6 is a fragmentary, side-elevational, exploded view of a portion of the apparatus partly in cross section and showing the specimen viewing assembly removed from the housing.
Figure 7:
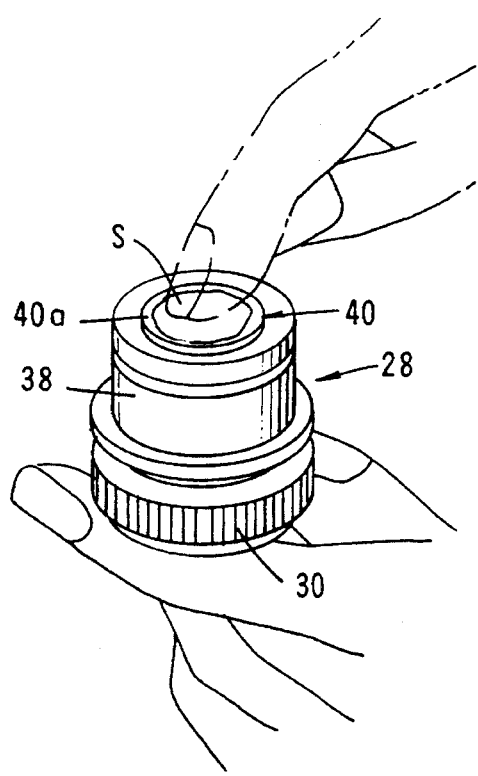
FIG. 7 is a generally perspective, illustrative view showing the manner in which saliva is deposited on the object slide of the specimen viewing assembly.

Referring to the drawings and particularly to FIGS. 1 through 8, one form of the apparatus of the present invention for determining the period of maximum fertility in women is there shown and generally identified by the numeral 20. The apparatus comprises a hand-held housing 22 having a body portion 22a and a base portion 22b (FIG. 2). As best seen by referring to FIG. 8, body portion 22a includes a generally cylindrically shaped wall 24 which defines an interior chamber 26 having a top opening 26a.

Disposed proximate the top of chamber 26 is magnification means for viewing the interior of chamber 26. In the present form of the invention, the magnification means comprises a support assembly 28 including an externally threaded, annular member 30 having a viewing aperture 32 which is sealed by a substantially transparent ocular eyepiece 34. Disposed within member 30 is a lens assembly comprising a ring shaped member 35 within which a pair of convex lenses 36a and 36b are mounted in a manner best seen in FIG. 8. The lenses preferably provide 40×±2× magnification when stacked and have a spherical accuracy of ±2%.

Removably receivable within top opening 26a is an internally threaded, generally ring-shaped member 38 which is adapted to threadably receive annular member 30 for movement of the lens assembly toward and away from a substantially transparent specimen slide or glass plate 40 which is connected to member 38. Plate 40 is provided with a substantially flat, smooth, saliva-receiving surface 40a.

It is to be understood that, while lenses 36a and 36b are shown as plano-convex lenses mounted with their convex surfaces in contact, various types of lenses in various configurations well known to those skilled in the art could be used in the present application. Similarly various types of ocular eyepieces and various kinds of specimen slides could be used.

Disposed internally of chamber 26 is illumination means for illuminating the interior of chamber 26. The illumination means here comprises a light source 46 such as a light emitting diode lamp which is disposed within chamber 26, a source of electrical energy, shown here as a pair of 1.5 volt lithium batteries 48a and 48b, and connector means for interconnecting lamp 46 with the electrical energy source or batteries 48a and 48b. In the form of the invention shown in FIGS. 1 through 8, the connector means comprises a readily, commercially available micro switch 50 having an operating plunger 52 extending from the base of the switch and through an opening provided in a base wall 25 of base portion 22b in the manner shown in FIGS. 3 and 8. Micro switch 50 is of a character well known to those skilled in the art such as is frequently used in computer circuits. Suitable switches are available from souces such as Dow Radio of Pasadena, Calif.

Figure 8:
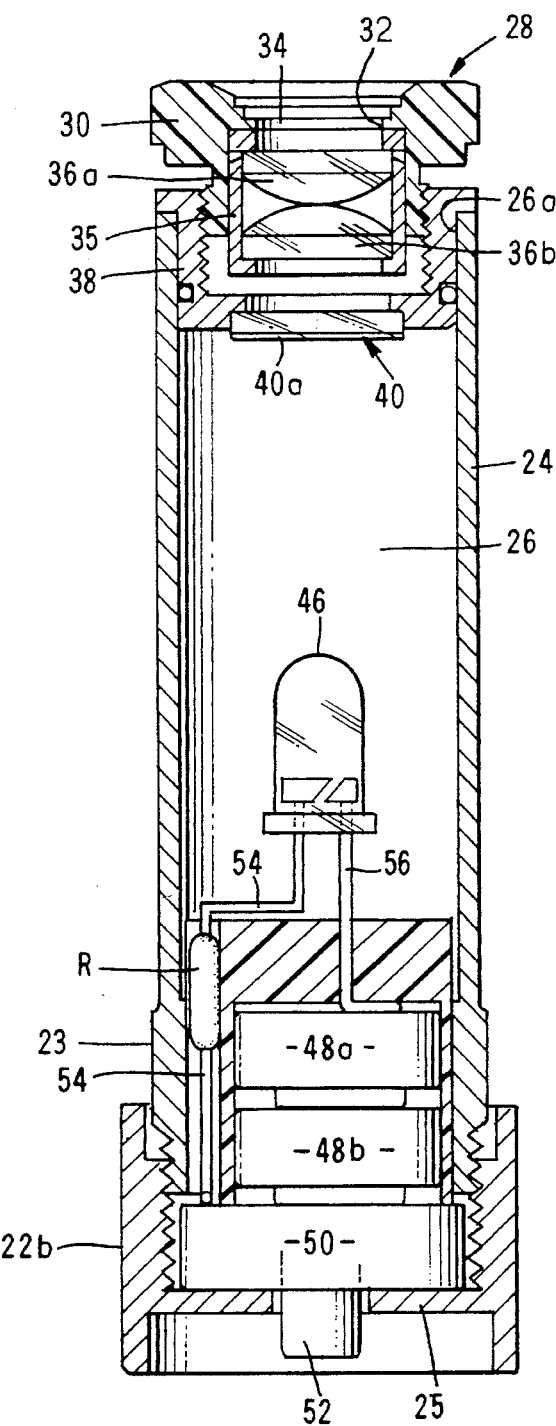
FIG. 8 is an enlarged cross-sectional view taken along lines 8—8 of FIG. 5.

An electrical connector or wire 54 connects a switch 50 with one terminal of lamp 46 via a ten ohm resister "R", while the other terminal 56 thereof is connected directly to the batteries. With this construction, depression of plunger 52 of switch 50 will connect lamp 46 with the electrical energy source thereby luminating lamp 46 and lighting the chamber 26. As shown in FIG. 8, body portion 22a is threadably interconnected with base 22b so as to permit access to switch 50 and to permit replacement of batteries 48a and 48b as may be required.

When the device is not in operation, a generally cylindrically shaped cap member 60 having a top wall 60a can be emplaced over body portion 22a in the manner shown in FIG. 1. Cover 60 is provided with a plurality of circumferentially spaced ribs 60b which frictionally engage enlarged diameter portion 23 of body portion 22a (see FIG. 4).

Figure 9:
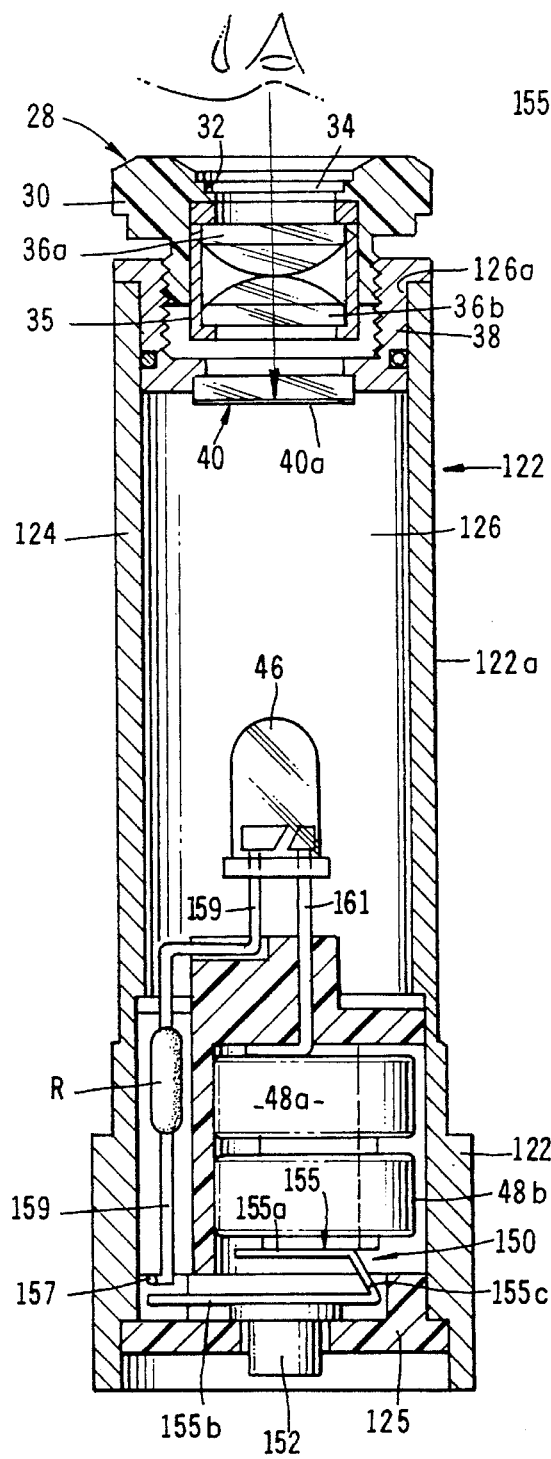
FIG. 9 is a side-elevational, cross-sectional view of an alternate form of the apparatus of the invention.
Figure 11:
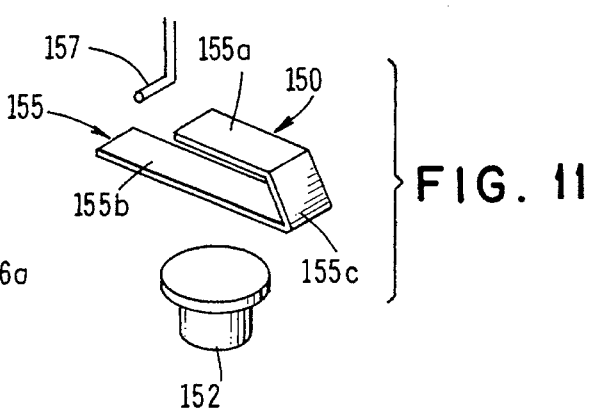
FIG. 11 is a generally perspective, exploded view of the switch assembly.
Figure 10:
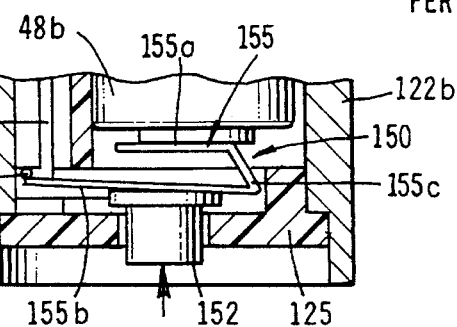
FIG. 10 is a fragmentary cross-sectional view illustrating the construction of the switch assembly of the apparatus shown in FIG. 9.

Turning next to FIGS. 9 through 11, an alternate form of the apparatus of the present invention is there shown. This apparatus is similar in most respects to that previously described and like numerals are used to describe like components. This latest form of the invention comprises a hand-held housing 122 having a body portion 122a and a base portion 122b (FIG. 9). Body portion 122a includes a generally cylindrically shaped wall 124 which defines an interior chamber 126 having a top opening 126a.

Disposed proximate the top of chamber 126 is magnification means for viewing the interior of chamber 126. This magnification means is identical in construction and operation to that described in connection with the embodiment shown in FIG. 1 through 8. Therefore, the details of its construction will not be repeated.

Mounted internally of chamber 126 is illumination means for illuminating the interior of chamber 126. The illumination means here comprises a lamp 46 which is disposed within chamber 126, a source of electrical energy, shown here as a pair of dry-cell batteries 48a and 48b, and connector means for interconnecting lamp 46 with the electrical energy source of batteries 48a and 48b. In the form of the invention shown in FIGS. 9, 10, and 11, the connector means comprises a spring type switch 150 having an operating plunger 152 extending from the base of the switch and through an opening provided in a base wall 125 of base portion 122b in the manner shown in FIGS. 9 and 10. Switch 150 is of a construction best seen in FIG. 11 and comprises, in addition to plunger 152, an electrically conductive spring member 155 having first and second legs 155a and 155b which are connected by a sloping segment 155c. Switch 150 also includes a generally "L" shaped contact 157 which forms a part of a connector lead 159 leading to lamp 46. A 10 ohm resister "R" is preferably disposed intermediate contact 157 and lamp 46.

Connector wire 159, its "L" shaped contact 157, and resister "R" comprise one lead to lamp 46 while the other lead, or wire 161, is connected directly to the batteries in the manner shown in FIG. 8. With this construction, depression of plunger 152 of the switch will cause leg 155b to engage contact with 157 against the biasing of leg 155c whereby lamp 46 will be connected to the electrical energy source via segment 155c and leg 155a thereby luminating lamp 46 and lighting the chamber 126. As shown in FIG. 9, body portion 122a, rather than being threadably interconnected with base 122b as in the first embodiment, is integrally formed therewith. With this construction, access to switch 150 and to batteries 48a and 48b is achieved by removing base plate 125 from base 122b and, via top opening 126a, pushing the components downwardly within chamber 126a.

As before, when the device is not in operation, a generally cylindrically shaped cap member 60 having a top wall 60a can be emplaced over body portion 22a in the manner shown in FIG. 1.

Considering now the method of the invention for determining the period of maximum fertility in women using the apparatus as described in the preceding paragraphs, the first step in the method involves the removal from top opening of the hand-held housing of the assembly comprising annular rings 28 and 38 within which the magnifying lenses are housed. Upon removal of this assemblage from the hand-held housing, the smooth surface 40a of the specimen slide 40 is exposed to view. This enables the deposition on the slide of a saliva specimen "S" from the woman being tested. After the saliva specimen has been allowed to dry to form a crystalline structure on the slide, the assemblage is reinserted into top opening of the hand-held housing. With the magnifying assemblage thus in place, an upward pressure exerted on the actuating plunger of either switch 50 or 150 will close the contact between the batteries and the lamp thereby energizing the lamp and illuminating the interior of chamber 26.

With chamber 26 illuminated, the user can view the specimen by looking through the eyepiece 34. By rotating annular member 28 relative to member 38, the magnifying means can be focused on the saliva specimen to clearly reveal the characteristics of the crystalline structure formed on the undersurface 40a of slide 40. If the user is unable to discern a specific crystalline pattern, then it will be necessary to remove the magnifying means assembly from the hand-held housing, carefully clean the specimen slide, and redeposit a fresh salvia specimen on the slide. If this deposition step is accomplished properly, after the saliva has dried, a clear crystalline pattern can be discerned by proper focusing of the magnifying means in the manner described.

Figure 12:
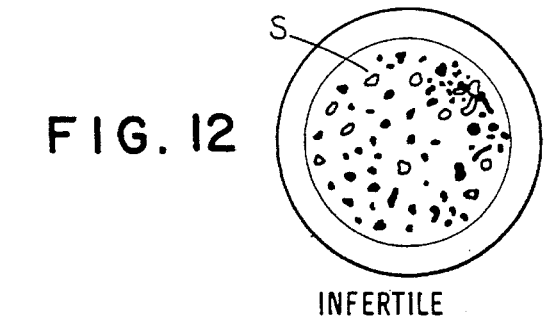
FIG. 12 is a diagrammatic view showing a standard comparison pattern for comparing therewith the appearance of the dried saliva on the object slide as viewed by the user of the apparatus.
Figure 13:
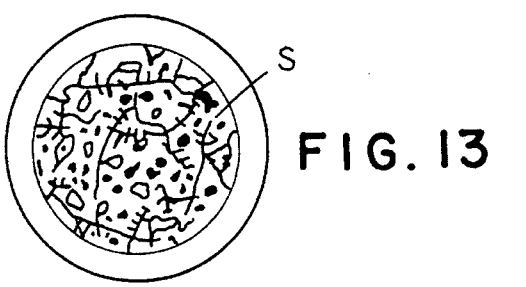
FIG. 13 is a diagrammatic view similar to FIG. 12 but showing another standard comparison pattern.
Figure 14:
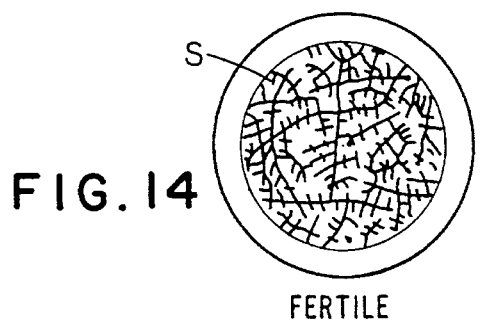
FIG. 14 is still another diagrammatic view showing still another standard comparison pattern.

Once the pattern as been observed, the user then compares the pattern being viewed with standard patterns of the character depicted in FIGS. 12, 13, and 14. During non-fertile days, the crystalline pattern should be random and comprise unconnected dots of the character shown in FIG. 12. However, if the pattern viewed on the specimen lens more closely resembles the pattern shown in FIG. 13, this would indicate that the woman is in a transition period, that is, in a period of less than maximum fertility, but in a period of time wherein conception may still be possible. If a fern structure of the character illustrated in FIG. 14 is viewed by the user by observing the specimen via the magnifying means, the user can conclude that the woman is in a period of maximum fertility. In this regard, studies have shown that fern structures of the character shown in FIG. 14 appear approximately three to four days before ovulation begins and end two to three days after it stops.

It is apparent that the user, by using the apparatus of the invention and by following the method described, can be accurately informed of her degree of fertility and can determine the optimum period at which she can conceive or, in the alternative, if she does not wish to conceive, the period of time during which she must be extra cautious, namely the period of maximum fertility as shown in FIG. 14 and the transitional period shown in FIG. 13.

After each use, the magnification assembly should be removed from the housing and carefully cleaned. After the magnifying assemblage is reinserted into the housing, cover 60 should be emplaced over the housing and the apparatus stored in a relatively temperature-constant, dust-free area.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for determining the period of maximum fertility in women comprising:
   (a) a hand-held housing having a base portion and a body portion connected to said base portion, said body portion having:
      (i) a wall defining an interior chamber having a top opening;
      (ii) a generally ring-shaped member removably receivable within said top opening of said interior chamber; and
      (iii) a transparent plate connected to said ring-shaped member; and
   (b) magnification means removably receivable within said top opening for viewing the interior of said chamber, said magnification means comprising:
      (i) a support assembly having a viewing aperture; and
      (ii) a magnifying lens mounted within said support assembly;
   (c) illumination means carried by said hand-held housing for illuminating said interior chamber; and
   (d) a saliva receiving surface disposed within said interior chamber intermediate said magnifying lens and said illumination means, said saliva receiving surface being formed in said transparent plate connected to said ring-shaped member.

2. An apparatus for determining the period of maximum fertility in women comprising:
   (a) a hand-held, generally cylindrically shaped housing having a base portion and a body portion connected to said base portion, said body portion including an interior chamber having a top opening;
   (b) a generally ring-shaped member removably receivable with said top opening of said chamber;
   (c) a substantially transparent plate connected to said ring-shaped member, said transparent plate having a saliva receiving surface;
   (d) magnification means receivable within said ring-shaped member for viewing the interior of said chamber, said magnification means comprising:
      (i) an annular-shaped support housing having a viewing aperture, said support housing being axially movable within said ring-shaped member; and
      (ii) a magnifying lens mounted within said support housing; and
   (e) illumination means disposed within said housing for illuminating said interior chamber thereof, said illumination means comprising:
      (i) an electric lamp disposed within said interior chamber of said hand-held housing;
      (ii) a battery disposed within said base portion of said hand-held housing; and
      (iii) connector means for interconnecting said electric lamp and said battery.

3. An apparatus as defined in claim 2, in which said connector means comprises a manually operated switch carried by said base portion of said hand-held housing for selectively interconnecting said battery with said electric lamp to illuminate said lamp.

4. An apparatus as defined in claim 3 in which said base portion has a base wall having an aperture and in which said switch includes a switch operating plunger extending through said aperture in said base wall.

5. An apparatus as defined in claim 4 in which said base portion of said hand-held housing is threadably connected to said body portion thereof.

6. An apparatus as defined in claim 5 further including a generally tubular shaped cover member removably interconnected with said hand-held housing for endorsing said body portion thereof.

7. A self-contained, portable apparatus for determining the period of maximum fertility in women comprising:
   (a) a hand-held, generally cylindrically shaped housing having a base portion and a body portion connected to said base portion, said body portion including an interior chamber having a top opening;
   (b) an internally threaded, generally ring-shaped member removably receivable with said top opening of said chamber;
   (c) a substantially transparent glass plate connected to said ring-shaped member, said plate having a flat, smooth, saliva-receiving surface;

(d) magnification means receivable within said ring-shaped member for viewing the interior of said chamber through said plate, said magnification means comprising:
  (i) an externally threaded, annular-shaped support housing having a viewing aperture, said support housing being threadably connected to said ring-shaped member for movement toward and away from said plate; and
  (ii) a magnifying lens mounted within said support housing; and
(e) illumination means disposed within said housing for illuminating said interior chamber thereof, said illumination means comprising:
  (i) a light emitting diode disposed within said interior chamber of said hand-held housing;
  (ii) a battery disposed within said base portion of said hand-held housing; and
  (iii) connector means for interconnecting said diode and said battery, said connector means comprising a manually operated switch carried by said base portion of said hand-held housing for selectively interconnecting said battery with said diode to illuminate said diode.

8. An apparatus as defined in claim 7 in which said base portion has a base wall having an aperture and in which said switch includes a switch operating member extending through said aperture in said base wall.

9. An apparatus as defined in claim 7 further including a substantially transparent ocular eyepiece sealably closing said viewing aperture of said annular-shaped support housing.

* * * * *